United States Patent [19]

DeBaun et al.

[11] 4,027,031

[45] May 31, 1977

[54] 2-CYCLOPROPANECARBOXAMIDO-S-HALOTHIAZOLE AS ANTI-INFLAMMATORY AGENTS

[75] Inventors: Jack R. DeBaun, Sunnyvale; Ferenc M. Pallos, Walnut Creek; Don R. Baker, Orinda, all of Calif.

[73] Assignee: Stauffer Chemical Company, Westport, Conn.

[22] Filed: Apr. 14, 1976

[21] Appl. No.: 676,770

Related U.S. Application Data

[63] Continuation-in-part of Ser. No. 572,241, April 28, 1975, abandoned.

[52] U.S. Cl. .................................................. 424/270
[51] Int. Cl.$^2$ ...................................... A61K 31/425
[58] Field of Search .................................... 424/270

Primary Examiner—Stanley J. Friedman
Attorney, Agent, or Firm—Edwin H. Baker

[57] ABSTRACT

2-Cyclopropanecarboxamido-S-halothiazole as anti-inflammatory agents.

5 Claims, No Drawings

2-CYCLOPROPANECARBOXAMIDO-S-HALO-THIAZOLE AS ANTI-INFLAMMATORY AGENTS

This application is a continuation-in-part of Serial No. 572,241, filed April 28, 1975, now abandoned.

This invention relates to 2-cyclopropanecarboxamido-S-halothiazole which is useful as anti-inflammatory agents.

The compounds, 2-cyclopropanecarboxamido-S-halothiazole, have the following structural formula:

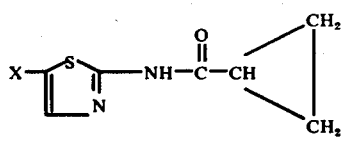

in which X is chloro, bromo, iodo or fluoro.

The compounds can be prepared according to the teaching of the following example.

EXAMPLE 2-cyclopropanecarboxamido-S-bromothiazole

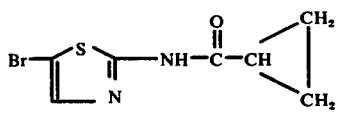

10.4 g (10.10 m) cyclopropanecarboxylic acid chloride was added to a stirred mixture of 16 ml (10.20 m) piperdine, 100 ml ethylenedichloride, and 25.9 g (0.10 m) 2-amion-S-bromothiozole hydrobromide over a period of 5 minutes with ice bath cooling to keep the temperature under 20° C. After standing for 15 minutes, the mixture was diluted with a 100 ml $H_2O$ to give a solid and 2 liquid phases. This mixture was diluted with 100 ml n-pentane and solid filtered off, washed with 100 ml water, and n-pentane to yield 16.5 g solid after drying in vacuo of the desired product. m.p. 211°–218° C.

The product of the example will hereinafter be called Compound Number 1. The corresponding chloro compound will hereinafter be called Compound Number 2.

Anti-Inflammatory Screening

The compounds of the present invention have pharmaceutical activity especially as anti-inflammatory agents. Anti-inflammatory activity is demonstrated by a test which involves the diminution of experimental edema induced in the hind paw of the rat by the injection of carrageenin.

Carrageenin injected into the foot of the rat produces an edematous condition which simulates part of the inflammatory process. Non-steroidal anti-inflammatory compounds inhibit the formation of this edema.

Methods and Procedures

The procedure used for measuring the inhibition of carrageenin-induced edema is a standard procedure well known in the pharmaceutical art and is as follows:

Male rats (Long Evans Strain) weighing between 130–200 grams are used in this assay. Five rats each are used in the treatment groups and in the known standard control; whereas ten rats are used in the control edema group. Unless otherwise indicated, phenylbutazone is administered orally at 100 mg/kg to the standard control group. The edema control group is administered the vehicle which consists of 0.25% methylcellulose solution. All of the rats are fasted for at least 15 hours prior to the test. Water is available ad libitum. All of the experimental drugs are given orally and are dissolved or suspended in 0.25% methylcellulose solution. One hour after administration of the test compound, 0.05 ml of a 1% sterile solution of carrageenin is injected into the plantar tissues of the left hind paw of each rat. Three hours after carrageenin administration, the paw volumes of injected paws are then measured by means of a water displacement apparatus. The apparatus used is a modification of that described by Adamkiewicz et al., Canadian Journal of Biochemistry and Physiology, 33: 332, 1955. The amount of edema is calculated and the percent reduction of edema from control values is determined. The mean volume of edema, based on 50 determinations, is 1.25 cc with a standard deviation of 0.226 cc. A reduction in edema greater than 25% of the control value is considered significant. Based on 46 determinations, phenylbutazone produced a mean inhibition of edema of 43.8% with a standard deviation of 13.4%.

We have found that the compounds of this invention produce a significant inhibition of induced edema in rats at a dose rate of 200 mg/kg.

Table I shows the reduction in edema in the hind paw of the rat according to the above-described test procedure, at 200 mg/kg unless otherwise indicated.

TABLE I

| Percent Reduction in Edema at 200 mg/kg | |
| --- | --- |
| Compound Number | Percent Reduction of Induced Edema |
| 1 | 51 |
| 2 | 50 |

The compounds of the present invention, either alone or in the form of pharmaceutical composition may be administered to an animal subject in any of a number of forms and via any of several routes. Thus, the compounds or compositions thereof may be orally administered in the form of tablets, pills, capsules, or in the form of a suspension. The compounds may also be administered parenterally in the form of an injectable solution or suspension. The compounds or compositions thereof may also be administered topically, in the form of an ointment or rectally, in the form of a suppository.

When orally administering the compounds or compositions, use can be made of a tablet, pill or capsule consisting entirely of the desired compound, although ordinarily, a composition comprising an effective amount of the compound and varying amounts of one or more physiologically inert materials such as carriers, vehicles, binders and the like will be used. Additionally, the compounds may be orally administered in the form of a suspension thereof in a suitable vehicle such as a syrup.

When parenterally administering the compounds or compositions, use may be made of a parenteral solution or suspension of the compound in a suitable solvent or suspension medium.

The compounds of the present invention may also be administered rectally in the form of a suppository comprising an effective amount of the desired compound and a suitable vehicle such as petroleum jelly.

Finally, the compounds of the present invention may be applied topically in the form of an ointment, salve, cream or lotion comprising an effective amount of the desired compound and a suitable vehicle such as petroleum jelly, etc.

We claim:

1. A method of treatment of an inflammatory condition in a mammal comprising administering to said mammal a therapeutically effective amount of 2-cyclopropanecarboxamido-5-halothiazole having the following structural formula:

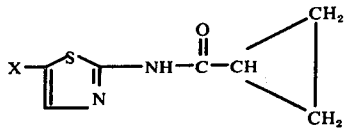

in which X is chloro, bromo, iodo or fluoro.

2. The method of claim 1 in which X is chloro.
3. The method of claim 1 in which X is bromo.
4. The method of claim 1 in which X is iodo.
5. The method of claim 1 in which X is fluoro.

* * * * *